United States Patent [19]

Seder et al.

[11] Patent Number: 5,041,101
[45] Date of Patent: Aug. 20, 1991

[54] HYSTERECTOMY DRAIN APPLIANCE

[75] Inventors: Edmund V. Seder, Santa Barbara; Richard E. Houts, Santa Ynez, both of Calif.

[73] Assignee: Helix Medical, Inc., Santa Barbara, Calif.

[21] Appl. No.: 361,325

[22] Filed: Jun. 5, 1989

[51] Int. Cl.5 .............................................. A61M 25/00
[52] U.S. Cl. .................................... 604/284; 604/264; 604/93
[58] Field of Search ............... 604/264, 284, 289, 177, 604/164, 281–283, 93, 7, 54, 55; 600/29

[56] References Cited

U.S. PATENT DOCUMENTS

| 3,800 | 10/1844 | Gale | 604/264 |
|---|---|---|---|
| 2,624,341 | 1/1953 | Wallace | 604/284 |
| 3,428,046 | 2/1969 | Remer et al. | 604/265 |
| 3,835,863 | 9/1974 | Goldberg et al. | 604/284 |
| 4,072,153 | 2/1978 | Swartz | 604/284 |
| 4,398,910 | 8/1983 | Blake et al. | 604/280 |
| 4,432,752 | 2/1984 | Marlon | 604/164 |
| 4,453,928 | 6/1984 | Steiger | 604/164 |
| 4,547,187 | 10/1985 | Kelly | 604/97 |
| 4,551,140 | 11/1985 | Shinohar | 604/280 |
| 4,654,032 | 5/1987 | Morales-George | 604/284 |
| 4,692,153 | 9/1987 | Berlin et al. | 604/280 |
| 4,734,094 | 3/1988 | Jacob et al. | 604/284 |
| 4,781,699 | 11/1988 | Suzuki et al. | 604/264 |
| 4,790,809 | 12/1988 | Kuntz | 604/280 |
| 4,883,474 | 11/1989 | Sheridan et al. | 604/280 |

FOREIGN PATENT DOCUMENTS 666090  7/1963  Canada ............................... 604/284

Primary Examiner—C. Fred Rosenbaum
Assistant Examiner—Daley, Kathleen A.
Attorney, Agent, or Firm—Marvin E. Jacobs

[57] ABSTRACT

A hollow, T-shaped body is connected to an extroducer rod by a flexible drain tube. The extroducer rod is longer than a human female vagina, sufficiently stiff to be passed therethrough when the vagina is in a collapsed state, and has a smooth rounded end to facilitate insertion through the vaginal cuff and passage through the vagina during an abdominal hysterectomy. The extroducer rod is also larger in diameter than a Foley catheter which is used to drain the bladder, and formed with external flutes which make it easily distinguishable from the catheter by feel. The T-shaped body has a leg which is connected to the drain tube, and two perpendicular arms. Drain holes are formed through the arms which open in a direction away from the leg. The innermost drain hole of each arm is cut away to a sufficient depth that the arms can collapse to positions parallel to the leg and drain tube to facilitate withdrawal of the body through the vagina. Notches having smooth, rounded walls are formed at desired spacings in the arms to facilitate trimming the arms to fit the patient's anatomy. The rounded walls of the notches and the location of the drain holes which face inwardly toward each other in the collapsed position of the arms prevents irritation of the vaginal wall by sharp edges during withdrawal.

16 Claims, 3 Drawing Sheets

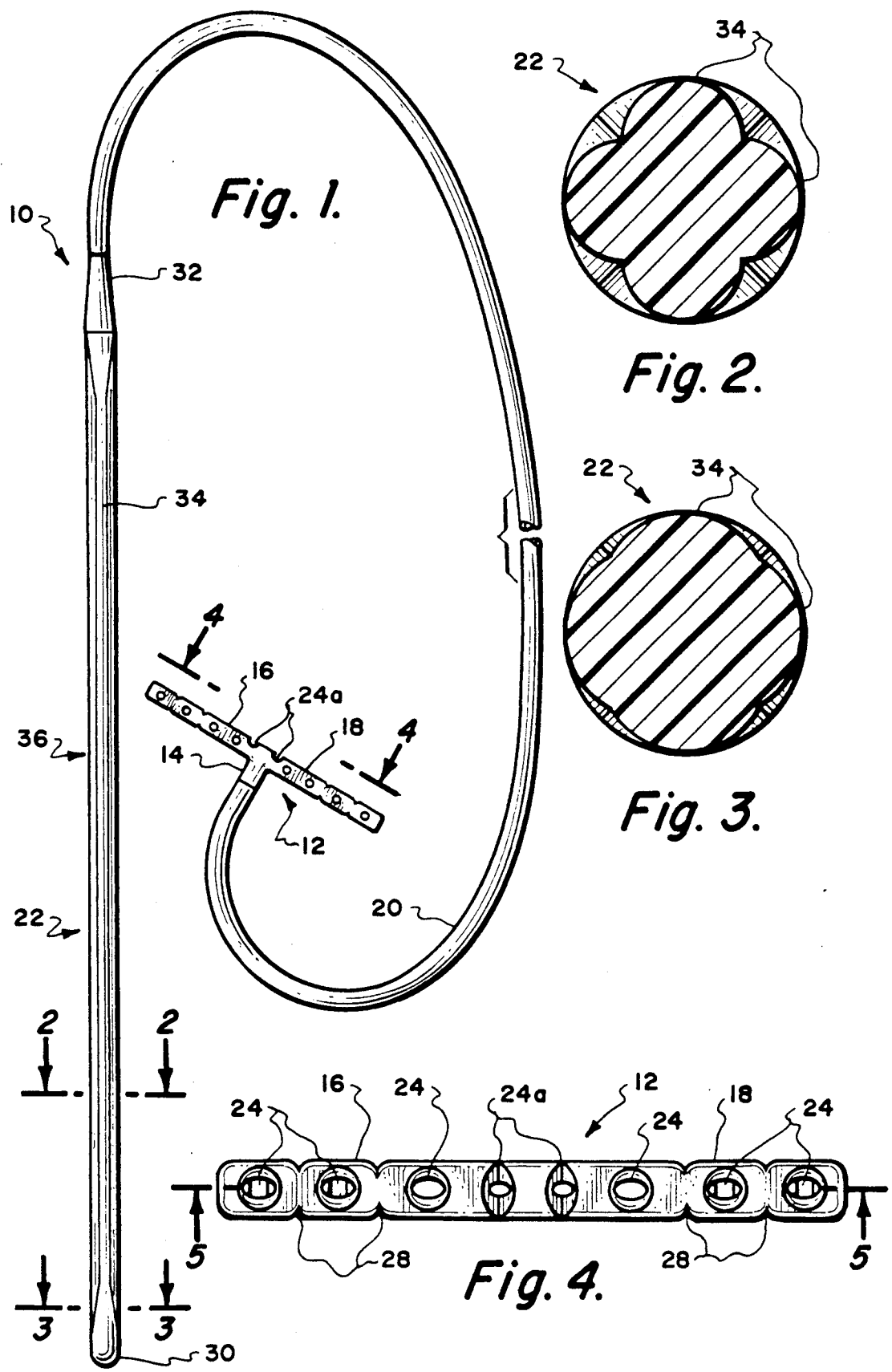

HYSTERECTOMY DRAIN APPLIANCE

TECHNICAL FIELD

The present invention relates to a device for postoperative draining of fluids from a patient and, more particularly, this invention relates to an improved drain for placement in the retroperitoneal space after hysterectomy.

BACKGROUND OF THE INVENTION

Hysterectomy is routinely performed in a potentially contaminated field due to the inability to completely sterilize the vagina. After removal of the uterus in either abdominal or vaginal hysterectomies, serum and blood collect in the retroperitoneal space. To lower the incidence of infection, most gynecologic surgeons insert a drain tube in this space, typically a Jackson-Pratt drain tube, to drain this fluid for about 72 hours after surgery. The tube is then removed by pulling the tube through the vagina. The Jackson-Pratt tube is in the form of a soft flexible T having a short top arm with drain holes and a long leg extending through the vagina, the end of which is connected to a drain pump.

Though effective in removing fluid from the retroperitoneal space, the Jackson-Pratt drain tube is difficult to insert and can cause irritation to sensitive tissue in the retroperitoneal space and the walls of the vagina, especially with older patients. Though the vaginal cuff differs from patient to patient, the Jackson-Pratt drain tube has a fixed geometry. If the upper arm is too short it can slip into the vaginal cuff. If it is too long, it can irritate tissue that it contacts. If the ends of the arms are trimmed, the sharp edges can irritate the vaginal walls when the drain tube is removed by pulling it through the vagina.

The drain holes are not uniformly spaced in the Jackson-Pratt drain and the device does not readily collapse when pulled, resulting in a Y-shaped configuration with the arms rubbing against the vaginal wall. Some of the drain holes on the lower surface of the arms are now disposed to the outside facing the vaginal wall and cause abrasion and irritation during removal.

The most serious problem is the difficulty in inserting the drain tube through the vagina. The surgery takes place in a sterile field. The vagina is a relatively collapsed tube with a soft curve running in a cephalo distal plane. The soft flexible tube must be pushed through collapsed tissue having a curved path. A further complexity is presented by the presence of an almost identical tube in shape and feel. During hysterectomy surgery a Foley catheter is passed through the uterus to drain fluid from the bladder of the patient.

The nurse must use a forceps to force the long leg of the drain tube through the vaginal cuff and far enough into the vagina to grasp the tip of the tube with her other gloved hand. This is very confusing to the nurse as she is extracting the long leg of the Jackson-Pratt drain by feel only and is unable to view the drain. The sharp end of the tube and the forceps can and do irritate tissue. The sterile field is violated with the glove and the forceps. The gloved hand working in the collapsed vagina does not have sensitive tactile feeling and it is common to mistake the similarly-sized Foley catheter for the Jackson-Pratt drain tube resulting in draining the bladder.

STATEMENT OF THE INVENTION

The hysterectomy drain device of the invention is easier to put in place by the surgical team and is softer and more comfortable for the patient. The device of the invention can be conformed to fit differing anatomies without fear of irritation and can be safely and easily introduced into and through the vagina without being mistaken with the Foley catheter tube and without irritation of the walls of the vagina.

The hysterectomy drain device of the invention includes an improved T-tube and a separate extroducer member. The T-tube can be readily modified to fit the geometry of the patient. The short arms contain curved circumferential indentations dividing the arms into lobes. By cutting the arms at any indentation a fresh curved end surface is formed. The arms contain evenly spaced holes promoting uniform and effective draining and do not contain drain holes on the posterior surface. A set of deep indentations, preferably oval, are provided on the anterior surface adjacent to the long leg which act as live hinges for the arms when the drain is removed by pulling on the long leg. The leg is usually at least 14 inches long to accommodate the maximum length of any normal vagina.

The drain device of the invention utilizes a separate introduction member called an "extroducer" connected to the end of the T-tube. The extroducer is a rod which is at least 14 inches long to enable it to travel the distance from the vaginal cuff to the exterior of the vagina. The extroducer is a smooth device which is stiffer than the drain tube, and has a rounded, leading face enabling smooth and comfortable insertion. Shaped side walls permit ready identification of the extroducer by a gloved hand of a nurse. The extroducer may be larger in diameter than the drain tube to further differentiate from the Foley catheter tube. This eliminates the blind groping with a gloved hand as practiced with the Jackson-Pratt drain tube. The relatively stiff, sterile extroducer rod can be held by its distal end and smoothly pushed into the vagina until it can be located. The extroducer is pulled through the vagina until its end emerges. The tube is gently pulled until the arms seat on the vaginal cuff. The end of the tube adjacent the extroducer is then cut and connected to the collection device such as a mini-hemovac, suction granade or a reservoir.

These and many other features and attendant advantages of the invention will become apparent as the invention becomes better understood by references to the following detailed description when considered in conjunction with the accompanying drawings.

BRIEF DESCRIPTION OF THE DRAWINGS

FIG. 1 is a plan view of a hysterectomy drain appliance embodying the present invention;

FIG. 2 is a transverse section taken on a line II—II of FIG. 1;

FIG. 3 is a transverse section taken on a line III—III of FIG. 1;

FIG. 4 is a plan view of an end of a T-shaped body of the drain appliance as designated at IV—IV in FIG. 1;

DETAILED DESCRIPTION OF THE INVENTION

Figure 5:
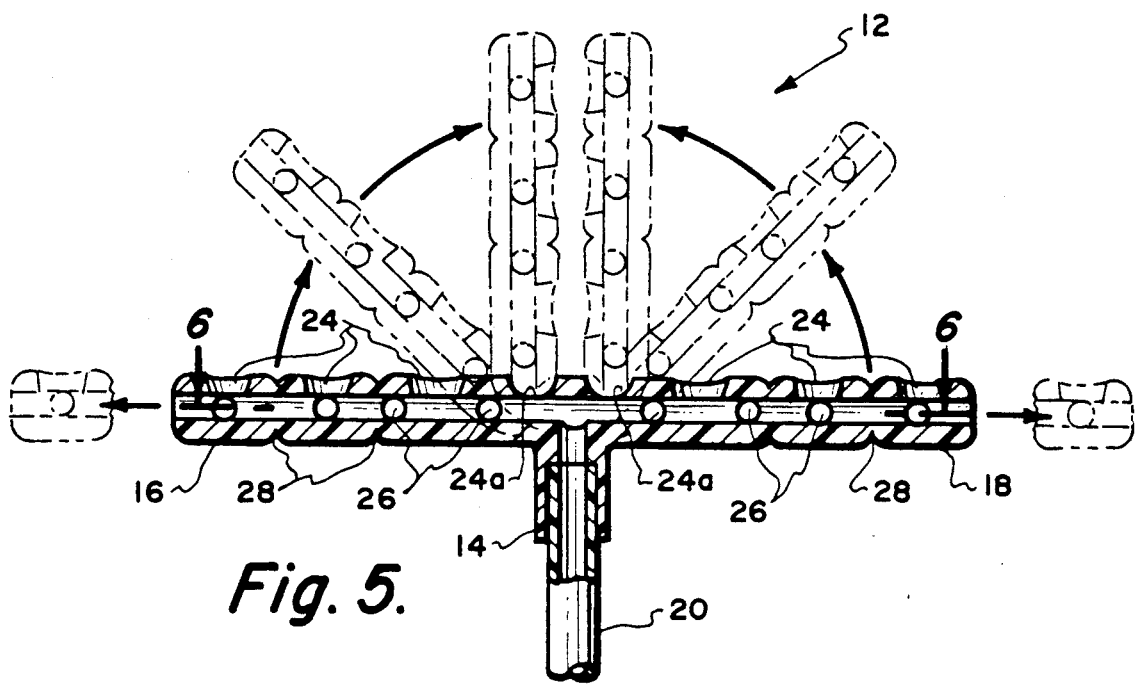
FIG. 5 is a longitudinal section taken on a line V—V of FIG. 4, further illustration a collapsed position of other appliance in phantom line.

Referring now to FIGS. 1 to 7 of the drawing, a hysterectomy drain appliance embodying the present invention is generally designated by the reference numeral 10 and includes a hollow, T-shaped body 12. The body 12 has a base leg 14 and arms 16 and 18 which extend perpendicularly outward from the base leg 14 in opposite directions. The end of the base leg 14 is connected through a flexible drain tube 20 to an extroducer rod 22.

Figure 6:
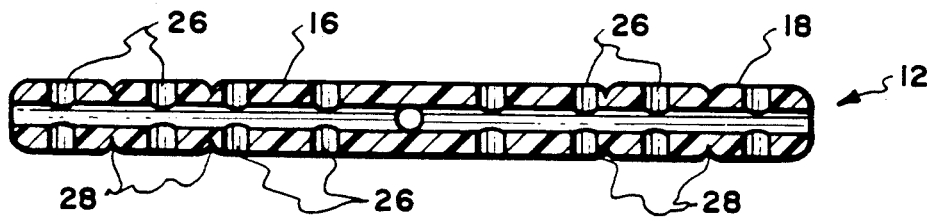
FIG. 6 is a transverse section taken on a line VI—VI of FIG. 5.

As best viewed in FIGS. 4 to 6, a plurality of drain holes 24 are formed through the surfaces of the arms 16 and 18 such that they open in a direction away from the base from the base leg 14. The two innermost drain holes of each arm 16 and 18, which are closest to the base leg 14, are further cut away as designated at 24a to a depth which is sufficient to enable the arms 16 and 18 to be resiliently bent or collapsed around the drain holes 24a as illustrated in phantom line in FIG. 5.

The arms 16 and 18 are further formed with drain holes 26 therethrough which open in a direction perpendicular to a plane (not designated) defined by the T-shape body 12. The arms 16 and 18 are yet further formed with a plurality of curcumferential indentations or notches 28 at desired spacings. In accordance with an important feature of the invention, the notches 28 are formed with smooth rounded walls as illustrated, which creates smooth, rounded ends of the arms 16 and 18 when the arms 16 and 18 are cut at the respective notches 28 respectively.

As illustrated in FIGS. 1 to 3, the extroducer rod 22 has a smooth rounded end 30 and an opposite end 32 which connects with the drain tube 20. The extroducer rod 22 is formed with longitudinally extending, external grooves which define rounded ridges or flutes 34 between the ends 30 and 32.

The extroducer rod 22 is sufficiently stiff as to be easily passed through a female human vagina which is in a collapsed state during a hysterectomy. The stiffness of the rod 22 may vary from completely rigid to substantially flexible within the scope of the invention. A desired degree of flexibility may be provided through selection of the material of the rod 22. Alternatively, flexibility may be provided by making the rod 22 taper inwardly from the ends 30 and 32 to a central portion 36 thereof as illustrated in FIG. 1 and also in the sectional views of FIGS. 2 and 3.

The T-shaped body 12, drain tube 20 and extroducer rod 22 are made of a material which can be easily and thoroughly sterilized, such as medical grade silicone. The extroducer rod 22 is sufficiently stiff as to facilitate insertion and passage through a collapsed female vagina which has a soft curve running in a cephalo distal plane. The rod 22 is long enough to extend completely through the vagina in the largest anatomy which may clinically be expected, and preferably has a length of approximately 14 inches. The diameter of the rounded end 30 of the extroducer rod 22 is preferably approximately 0.375 inch.

The diameters of the base leg 14 and arms 16 and 18 of the T-shaped body 12 as well as the drain tube 20 are preferably approximately 0.25 inch. The drain tube 20 is preferably 24 inches long. The T-shaped body 12 may be rigid, but is preferably soft and resilient, and sufficiently stiff to prevent collapse and to retain the T-shaped configuration until removal and folding as aided by the live hinge arrangement at the drain holes 24a.

Figure 7:
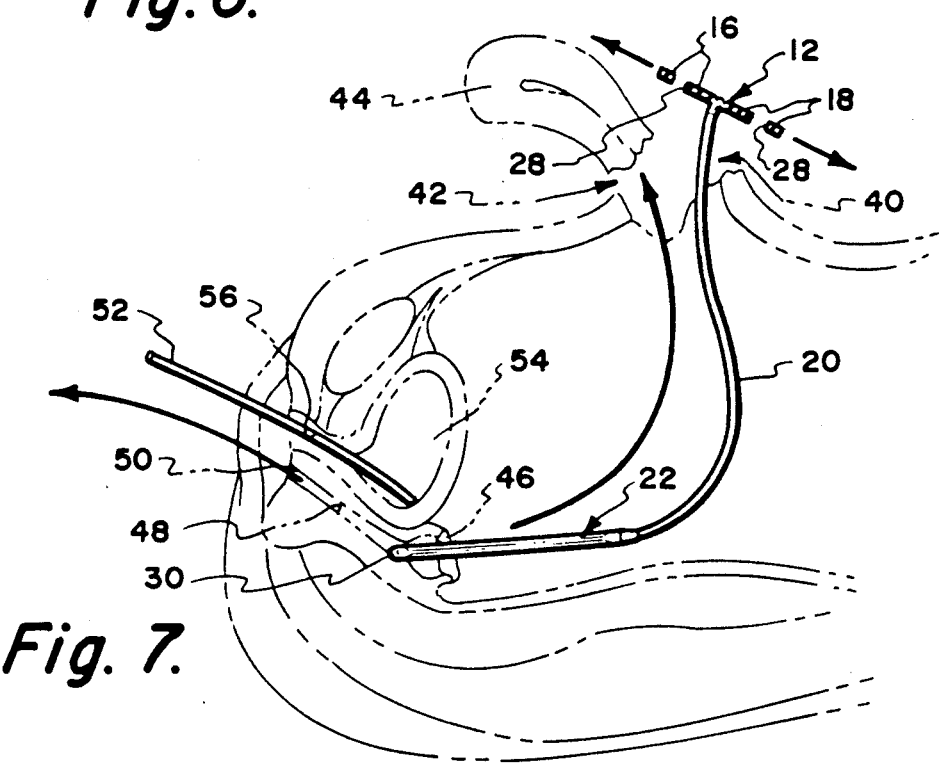
FIGS. 7 to 9 are diagrams illustrating the use of the present appliance during an abdominal hysterectomy.
Figure 8:
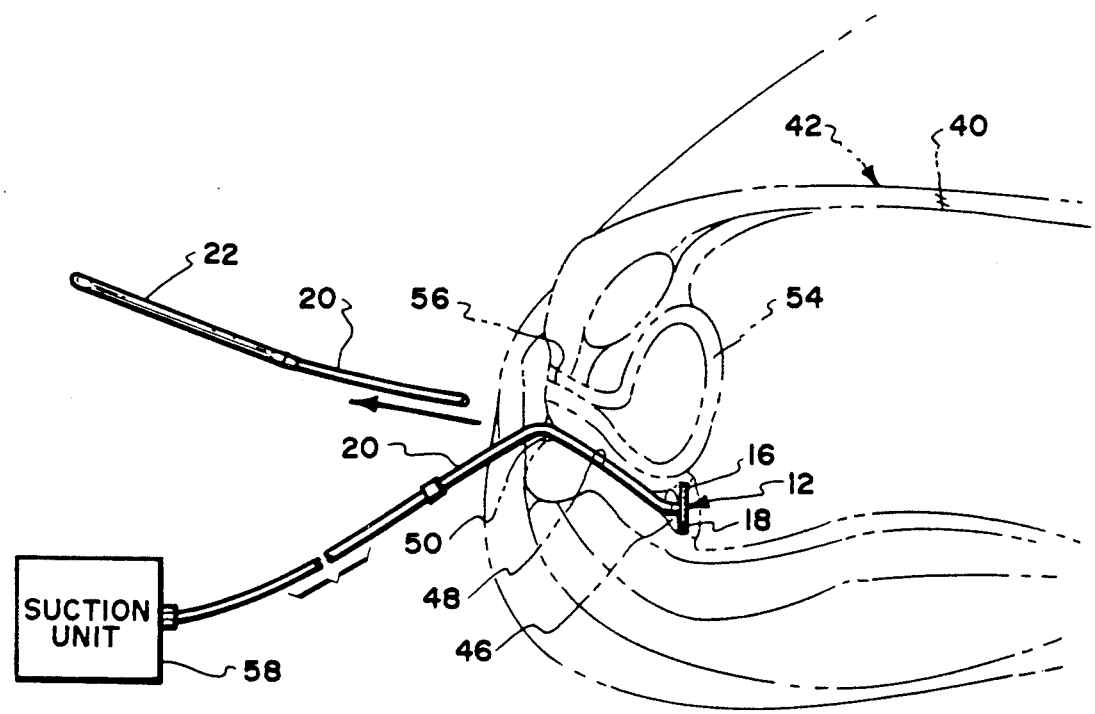
Figure 9:
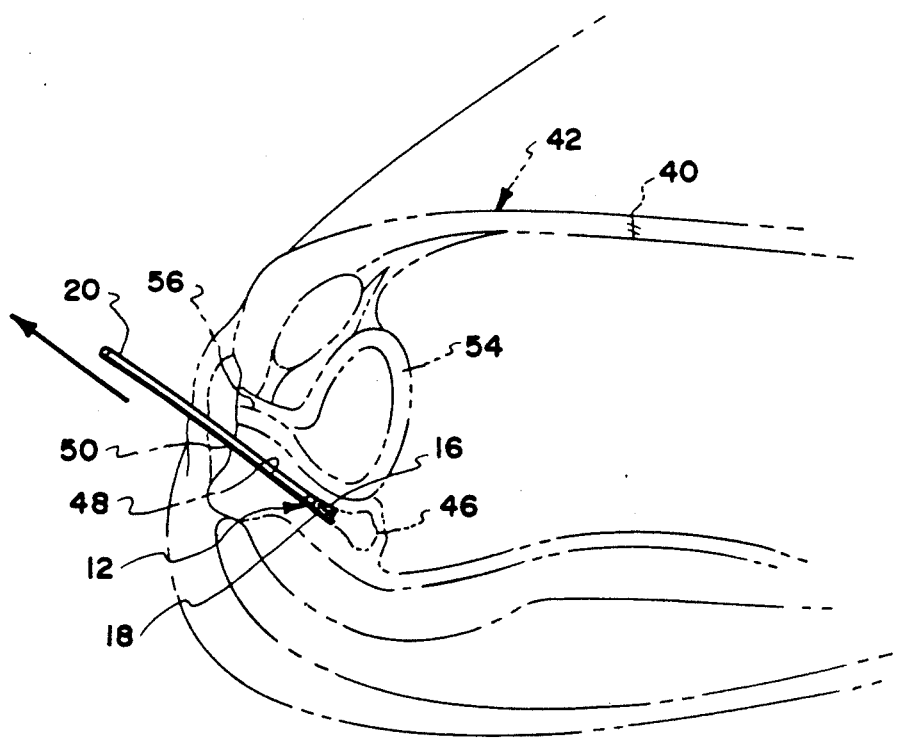

The use of the hysterectomy drain appliance 10 in an abdominal hysterectomy in accordance with the present invention is illustrated in FIGS. 7 to 9. As viewed in FIG. 7, an incision 40 is made through the abdominal area 42 of the patient, a uterus 44 is removed, and a cuff 46 of a vagina 48 is sutured and prepared in the normal manner. The extroducer rod 22 is introduced through the cuff 46 and passed through the vagina 48 so that the rounded end 30 and adjacent portion of the extroducer rod 22 protrude through an orifice 50 of the vagina 48. Further illustrated is a Foley catheter 52 which passes through a urethra 56 for drainage of a bladder 54.

In accordance with an important feature of the invention, the extroducer rod 22 is sufficiently larger in diameter and provided with the flutes 34 so that it is easily distinguishable from the catheter 52 by feel.

As viewed in FIG. 8, the arms 16 and 18 are trimmed at the desired notches 28 in accordance with the particular anatomy of the patient. The protruding end 30 and adjacent portion of the extroducer rod 22 are identified, and the extroducer rod 22 is slowly withdrawn through the vagina 48 until the arms 16 and 18 of the body 12 rest at the vaginal cuff 46. Repair of the peritoneum is completed and the incision 40 is closed. Following placement of the body 12, the extroducer rod 22 is cut from the drain tube 20, and the drain tube 20 is attached to a reservoir, mini-hemovac or other suction unit 58 to perform the desired drainage of the retroperitoneal space.

The appliance 10 is typically utilized as illustrated in FIG. 8 for a period of approximately 72 hours, after which time it is removed as shown in FIG. 9. Steady, gentle traction is exerted on the drain tube 20 which causes the T-shaped body 12 to be withdrawn through the cuff 46 and vagina 48. The depth of the cut away drain holes 24a is sufficient that the arms 16 and 18 will resiliently bend or collapse parallel to the drain tube 20, thereby offering only minimal resistance to withdrawal of the body 12. The rounded walls of the notches 28 and the location of the drain holes 24 which face inwardly toward each other in the collapsed position of the arms 16 and 18 prevent irritation of the vaginal wall by sharp edges during withdrawal.

Although not illustrated, the present hysterectomy drain appliance may also be used for vaginal hysterectomies, in which case the extroducer rod 22 is not required. In such an application, the uterus is removed and the peritoneum is closed in the usual manner. The vaginal cuff 46 may be closed except for the central 2 centimeters. After trimming the arms 16 and 18 of the body 12 to fit the patient's anatomy, the T-shaped body 12 may be inserted through the orifice 50 of the vagina 48 using long thumb forceps. In this case, the forceps bend and clamp the arms 16 and 18 against the base leg 14 and drain tube 20 (opposite to the direction shown in FIG. 5). After the body 12 has been passed through the vagina 48 to an extent which is sufficient for the arms 16 and 18 to completely protrude through the cuff 46, the forceps are retracted and the arms 16 and 18 allowed to resiliently spring outwardly to their operative positions as viewed in FIG. 8. The suction unit 58 is then attached to the drain tube 20 as in the case of the abdominal hysterectomy.

While an illustrative embodiment of the invention has been shown and described, numerous variations and alternate embodiments will occur to those skilled in the art, without departing from the spirit and scope of the invention. Accordingly, it is intended that within the scope of the appended claims, the present invention may be practiced otherwise than as specifically described.

It is to be realized that only preferred embodiments of the invention have been described and that numerous substitutions, modifications and alterations are permissible without departing from the spirit and scope of the invention as defined in the following claims.

What is claimed is:

1. A hysterectomy drain appliance comprising:
a hollow T-shaped body having a base leg and two arms extending perpendicularly outward from the base leg in opposite directions;
an extroducer rod; and
a flexible drain tube connecting an end of the base leg with an end of the extroducer rod;
each arm being formed with a plurality of drain holes therethrough opening away from the base leg;
the extroducer rod being longer than a human female vagina, and having a smooth rounded end opposite the end which connects with the drain tube.

2. An appliance according to claim 1, in which one of the drain holes of each arm located closest to the base leg is cut away to a sufficient depth that the arms may be resiliently bent therearound to positions substantially parallel to the base leg.

3. An appliance according to claim 2, in which each arm is further formed with at least one notch having smooth, rounded walls.

4. An appliance according to claim 1, in which at least a portion of the extroducer rod extending from the rounded end is formed with external ridges of sufficient height to be identifiable by feel.

5. An appliance as in claim 1, in which the rounded end of the extroducer rod is sufficiently larger in diameter than a Foley catheter as to be distinguishable therefrom by feel.

6. An appliance as in claim 1, in which the rounded end of the extroducer rod is approximately 0.375 inches in diameter.

7. An appliance as in claim 1, in which the external ridges of the extroducer rod comprise longitudinal flutes.

8. An appliance as in claim 1, in which the extroducer rod is tapered inwardly from said ends to a central portion thereof.

9. An appliance as in claim 1, in which the extroducer rod is approximately 14 inches long.

10. An appliance as in claim 1, in which the arms are further formed with a plurality of drain holes therethrough opening perpendicular to a plane defined by the base leg and arms.

11. An appliance as in claim 1, in which the T-shaped body is substantially rigid except at said cut away drain holes.

12. A hollow, T-shaped body for a hysterectomy drain appliance having a base leg with an end formed with a drain tube connector and two arms extending perpendicularly outward from the base leg in opposite direction;
each arm having a top surface facing the base leg; a bottom surface and side surfaces;
each arm being formed with a plurality of drain holes therethrough in said bottom surface and said side surfaces opening away from the base leg and being absent drain holes in the top surface facing the base leg; one of the drain holes in said bottom surface of each leg which is located closest to the base leg being cut away deeper than said drain holes to a sufficient depth that the arms may be resiliently bent therearound to positions substantially parallel to the base leg such that said top surface which is absent drain holes is opposite vaginal tissue.

13. A body as in claim 14 in which each arm contains a plurality of said circumferential notches.

14. A body as in claim 12 in which each arm is further formed with at least one circumferential notch parallel to the base leg and said notch having smooth, rounded walls.

15. A body as in claim 12, being substantially rigid except at said cut away drain holes.

16. A body as in claim 12, in which the base leg and arms are approximately 0.25 inch in diameter.

* * * * *